(12) United States Patent
Etou et al.

(10) Patent No.: US 9,988,328 B2
(45) Date of Patent: Jun. 5, 2018

(54) METHOD FOR PRODUCING FLUORINATED METHANE

(71) Applicant: DAIKIN INDUSTRIES, LTD., Osaka (JP)

(72) Inventors: Yuusuke Etou, Osaka (JP); Shingo Nakamura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days. days.

(21) Appl. No.: 15/520,876

(22) PCT Filed: Oct. 22, 2015

(86) PCT No.: PCT/JP2015/079813
§ 371 (c)(1),
(2) Date: Apr. 21, 2017

(87) PCT Pub. No.: WO2016/063939
PCT Pub. Date: Apr. 28, 2016

(65) Prior Publication Data
US 2017/0334814 A1 Nov. 23, 2017

(30) Foreign Application Priority Data

Oct. 23, 2014 (JP) .................................. 2014-216193

(51) Int. Cl.
| C07C 19/08 | (2006.01) |
| C07C 43/12 | (2006.01) |
| B01J 27/12 | (2006.01) |
| B01J 21/04 | (2006.01) |
| B01J 23/26 | (2006.01) |
| B01J 23/06 | (2006.01) |
| B01J 21/06 | (2006.01) |

(52) U.S. Cl.
CPC .............. *C07C 19/08* (2013.01); *C07C 43/12* (2013.01); *B01J 21/04* (2013.01); *B01J 21/063* (2013.01); *B01J 23/06* (2013.01); *B01J 23/26* (2013.01); *B01J 27/12* (2013.01)

(58) Field of Classification Search
CPC ..... C07C 17/361; C07C 17/383; C07C 51/64; C07C 17/38; C07C 41/06; C07C 19/08
See application file for complete search history.

(56) References Cited

U.S. PATENT DOCUMENTS

2013/0012740 A1 1/2013 Okamoto et al.
2015/0299088 A1 10/2015 Nakamura et al.

FOREIGN PATENT DOCUMENTS

| JP | 56-40617 | 4/1981 |
| JP | 2000-95714 | 4/2000 |
| JP | 2014-114277 | 6/2014 |
| WO | 2011/102268 | 8/2011 |

OTHER PUBLICATIONS

Takat et al, JP 2012-180285, machine transtion, Sep. 20, 2012.*
International Search Report dated Nov. 24, 2015 in International (PCT) Application No. PCT/JP2015/079813.
Decision to Grant a Patent dated Jan. 29, 2016 in corresponding Japanese Application No. 2014-216193, with translation.
Notification of Reasons for Refusal dated Nov. 13, 2015 in corresponding Japanese Application No. 2014-216193, with translation.
Written Amendment filed Jan. 18, 2016 in corresponding Japanese Application No. 2014-216193, with translation.
Written Argument filed Jan. 18, 2016 in corresponding Japanese Application No. 2014-216193, with translation.

* cited by examiner

*Primary Examiner* — Jafar Parsa
(74) *Attorney, Agent, or Firm* — Wenderoth, Lind & Ponack, L.L.P.

(57) ABSTRACT

An object of the present invention is to extend the catalyst lifetime in a method for producing fluoromethane by pyrolyzing fluorine-containing methyl ether in the presence of a catalyst. The present invention provides a method for producing fluoromethane by pyrolyzing a fluorine-containing methyl ether represented by Formula (1) in a gas phase in the presence of a catalyst,
the pyrolysis being conducted at a moisture concentration of 100 ppm or less,

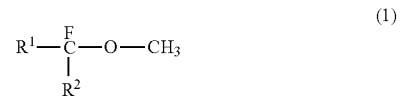

(1)

wherein $R^1$ and $R^2$ are identical or different, and each represents a substituted or unsubstituted straight or branched monovalent aliphatic hydrocarbon group, substituted or unsubstituted monovalent aromatic hydrocarbon group, substituted or unsubstituted monovalent cyclic aliphatic hydrocarbon group, hydrogen atom, or halogen atom.

9 Claims, No Drawings

METHOD FOR PRODUCING FLUORINATED METHANE

TECHNICAL FIELD

The present invention relates to a method for producing fluoromethane, which is useful as a dry etching gas.

BACKGROUND ART

Hydrofluorocarbons are useful as an etching gas for the microfabrication of semiconductors, liquid crystals, etc. In particular, fluoromethane ($CH_3F$) has been attracting attention as an etching gas for forming state-of-the-art microstructures.

A known method for producing fluoromethane comprises pyrolyzing fluorine-containing methyl ether in the presence of a catalyst (Patent Literature 1 and Patent Literature 2).

CITATION LIST

Patent Literature

PTL 1: WO 2011/102268
PTL 2: JP2014-114277A

SUMMARY OF INVENTION

Technical Problem

An object of the present invention is to extend the catalyst lifetime in a previously known method for producing fluoromethane by pyrolyzing fluorine-containing methyl ether in the presence of a catalyst.

Solution to Problem

The present inventors conducted extensive research to achieve the above object. As a result, the inventors found that pyrolysis under dehydration conditions enables extension of catalyst lifetime. The inventors conducted further research based on these findings. The present invention has thus been accomplished.

More specifically, the present invention encompasses the following embodiments.

Item 1. A method for producing fluoromethane by pyrolyzing a fluorine-containing methyl ether represented by Formula (1) in a gas phase in the presence of a catalyst, the pyrolysis being conducted at a moisture concentration of 100 ppm or less,

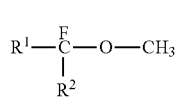

(1)

wherein $R^1$ and $R^2$ are identical or different, and each represents a substituted or unsubstituted straight or branched monovalent aliphatic hydrocarbon group, substituted or unsubstituted monovalent aromatic hydrocarbon group, substituted or unsubstituted monovalent cyclic aliphatic hydrocarbon group, hydrogen atom, or halogen atom.

Item 2. A method for producing fluoromethane by pyrolyzing a fluorine-containing methyl ether represented by Formula (1) above in the presence of a catalyst, the method comprising the step of removing moisture from the reaction system before or simultaneously with pyrolysis.

Item 3. The method according to Item 1 or 2, wherein the catalyst is at least one member selected from the group consisting of metal oxides, fluorinated metal oxides, and metal fluorides.

Item 4. The method according to any one of Items 1 to 3, wherein the catalyst is at least one member selected from the group consisting of alumina, chromium oxide, titanium oxide, zinc oxide, fluorinated alumina, fluorinated chromium oxide, fluorinated titanium oxide, fluorinated zinc oxide, $AlF_3$, $TiF_4$, $CrF_3$, and $ZnF_2$.

Item 5. The method according to Item 1 or 2, wherein the catalyst is alumina.

Item 6. The method according to Item 4 or 5, wherein the alumina is γ-alumina.

Item 7. The method according to any one of Items 3 to 6, wherein the catalyst has a pore volume of 0.5 ml/g or more.

Item 8. The method according to any one of Items 1 to 7, wherein the temperature of the pyrolysis reaction is 100 to 400° C.

Item 9. The method according to any one of Items 1 to 8, wherein the pressure during the pyrolysis reaction is 0.05 to 1 MPa.

Item 10. The method according to any one of Items 1 to 9, wherein the pyrolysis is performed in the presence of at least one gas selected from the group consisting of hydrogen fluoride, chlorine, hydrogen chloride, and air.

Item 11. The method according to Item 10, wherein the pyrolysis is performed in the presence of the gas at a volume ratio of 0.03 or more relative to the fluorine-containing methyl ether being taken as 1.

Item 12. The method according to Item 10 or 11, comprising the step of adding at least one gas selected from the group consisting of hydrogen fluoride, chlorine, hydrogen chloride, and air, to the reaction system before or simultaneously with the pyrolysis.

Item 13. The method according to Item 12, wherein the step is for adding the gas at a volume ratio of 0.03 or more relative to the fluorine-containing methyl ether being taken as 1.

Advantageous Effects of Invention

According to the present invention, it is possible to extend the catalyst lifetime in a method for producing fluoromethane by pyrolyzing fluorine-containing methyl ether in the presence of a catalyst. In other words, the same amount of fluoromethane is obtained with a smaller amount of catalyst, compared with previously known methods. The present invention is thus advantageous.

DESCRIPTION OF EMBODIMENTS

1. Starting Compound

In the present invention, a fluorine-containing methyl ether represented by Formula (1) is used as a starting material:

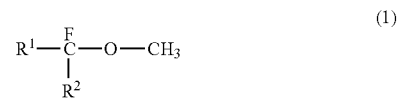

(1)

wherein $R^1$ and $R^2$ are identical or different, and each represents a substituted or unsubstituted straight or branched monovalent aliphatic hydrocarbon group, substituted or unsubstituted monovalent aromatic hydrocarbon group, substituted or unsubstituted monovalent cyclic aliphatic hydrocarbon group, hydrogen atom, or halogen atom.

There is no particular limitation on the method for producing fluorine-containing methyl ether used as a starting material, and compounds obtained by any method may be used.

In Formula (1) above, $R^1$ and $R^2$ are preferably identical or different, and each represents a substituted or unsubstituted $C_{1-30}$ straight or branched monovalent aliphatic hydrocarbon group, substituted or unsubstituted $C_{6-12}$ monovalent aromatic hydrocarbon group, or substituted or unsubstituted $C_{6-12}$ monovalent cyclic aliphatic hydrocarbon group. More preferably, $R^1$ and $R^2$ are identical or different, and each represents a substituted or unsubstituted $C_{1-10}$ straight or branched monovalent aliphatic hydrocarbon group, substituted or unsubstituted $C_{6-10}$ monovalent aromatic hydrocarbon group, or substituted or unsubstituted $C_{6-10}$ monovalent cyclic aliphatic hydrocarbon group.

Examples of $C_{1-10}$ straight or branched monovalent aliphatic hydrocarbon group include, but are not particularly limited to, $C_{1-10}$ alkyl groups.

Specific examples of $C_{1-10}$ alkyl groups include methyl, ethyl, trimethyl, propyl, 2-methylethyl, hexyl, octyl, and the like.

Of $C_{1-10}$ alkyl groups, $C_{1-6}$ alkyl groups are preferable, alkyl groups are more preferable, and $C_{1-3}$ alkyl groups are even more preferable.

Examples of $C_{6-10}$ monovalent aromatic hydrocarbon groups include, but are not particularly limited to, phenyl, methylphenyl, ethylphenyl, and the like.

Examples of $C_{6-10}$ monovalent cyclic aliphatic hydrocarbon groups include, but are not particularly limited to, cyclohexyl, methyl cyclohexyl, ethyl cyclohexyl, and the like.

In the above, at least one hydrogen atom or all of the hydrogen atoms of the monovalent aliphatic hydrocarbon group, monovalent aromatic hydrocarbon group, or monovalent cyclic aliphatic hydrocarbon group may be substituted with at least one heteroatom selected from the group consisting of fluorine, chlorine, and bromine.

In the above, halogen is preferably fluorine, chlorine, and bromine, and more preferably fluorine.

Specific examples of compounds usable as a starting material include, but are not particularly limited to, 1,1,3,3,3-pentafluoro-2-trifluoromethylpropylmethyl ether, and the like.

In particular, perfluoroisobutylene $((CF_3)_2C=CF_2)$, which is a by-product from production of hexafluoropropene used as a starting material of fluororesin, has until now been discarded as waste; however, when reacted with methanol, perfluoroisobutylene yields 1,1,3,3,3-pentafluoro-2-trifluoromethylpropyl methyl ether. Use of the thus-obtained 1,1,3,3,3-pentafluoro-2-trifluoromethylpropyl methyl ether as a starting material in the present invention allows for effective utilization of waste and enables the desired product to be produced inexpensively by using a low-cost starting material. In the present invention, phrases stating that 1,1,3,3,3-pentafluoro-2-trifluoromethylpropyl methyl ether used as a starting material is obtained by reacting perfluoroisobutylene and methanol are limited to the meaning that the 1,1,3,3,3-pentafluoro-2-trifluoromethylpropyl methyl ether is obtained by that reaction, and is not obtained by any other method. The method for obtaining 1,1,3,3,3-pentafluoro-2-trifluoromethylpropyl methyl ether by reacting perfluoroisobutylene and methanol is a known method and may be conducted in accordance with known reaction conditions. For example, the reaction may be performed in accordance with the method disclosed in JP2001-506261A.

2. Pyrolysis Reaction Method

As a starting material, the method of the present invention uses the fluorine-containing methyl ether mentioned above, and the method performs a pyrolysis reaction in a gas phase in the presence of a catalyst.

(1) Catalyst

The catalyst is not particularly limited as long as it is active for a pyrolysis reaction in a gas phase. Examples of the catalysts include metal oxides, fluorinated metal oxides, metal fluorides, and the like. These may be used singly or in a combination of two or more.

Of these, preferable examples of metal oxides include alumina, chromium oxide, titanium oxide, zinc oxide, and the like. In addition, fluorinated metal oxides obtained by fluorinating part of these metal oxides may be used. The fluorinated metal oxide catalysts may be those obtained by fluorinating a metal oxide catalyst with hydrogen fluoride or the like beforehand, or metal oxide catalysts that are partly fluorinated in the reaction process of the production method of the present invention. Preferable examples of metal fluorides include $AlF_3$, $TiF_4$, $CrF_3$, $ZnF_2$, and the like.

Among metal oxides, alumina is preferable, and α-alumina, activated alumina, etc., may be used. Examples of usable activated alumina include ρ-alumina, χ-alumina, κ-alumina, η-alumina, pseudo-γ-alumina, γ-alumina, δ-alumina, θ-alumina, and the like. Of these, γ-alumina and η-alumina are preferable, and γ-alumina is particularly preferable. Silica alumina ($SiO_2/Al_2O_3$), a composite oxide, may also be used as a catalyst. The proportion of silica $SiO_2$ in silica alumina is preferably 20 to 90 wt %, and more preferably 50 to 80 wt %.

The larger the pore volume of the catalyst, the higher the activity. The pore volume of the catalyst is preferably 0.4 ml/g or more, and particularly preferably 0.5 ml/g or more. The upper limit of the pore volume of the catalyst is not particularly limited, and is typically 5 ml/g or less, and, in terms of reaction rate and catalyst strength, preferably 2 ml/g or less. The pore volume may be measured by a gas adsorption method, a mercury intrusion method, or the like.

On the catalyst may be deposited an alkali metal or alkaline earth metal fluoride, such as KF, NaF, and $MgF_2$.

There is no particular limitation on the method for obtaining the fluorinated metal oxides mentioned above. For example, the fluorinated metal oxides may be obtained by bringing the metal oxides described above into contact with anhydrous hydrogen fluoride or Freon® while heating to allow a fluorination reaction to proceed. The method for bringing the metal oxides into contact with hydrogen fluoride is not particularly limited and may be a continuous flow method in which hydrogen fluoride is allowed to flow through a reaction tube containing the catalyst or a batch method in which hydrogen fluoride or Freon® is enclosed in a container containing the catalyst. In particular, the flow method is preferable in terms of a short treatment time.

The Freon® is preferably one with a large number of fluorine atoms and a small number of carbon atoms. Examples of Freon® include trifluoromethane, difluorochloromethane, octafluoroethane, and the like.

The degree of fluorination of a metal oxide is not particularly limited; those having a fluorine content of about 5 to 50 wt % based on the total weight of fluorinated metal oxide are preferably used.

The temperature of the fluorination treatment for a metal oxide is preferably higher than that of the pyrolysis reaction described below and is, for example, preferably about 150 to 500° C., more preferably about 200 to 400° C., and even more preferably about 250 to 350° C. An excessively low temperature in the fluorination treatment decreases the effect of the catalyst because of insufficient fluorination, whereas an excessively high temperature in the fluorination treatment additionally requires a heat-resistant material. Thus, an excessively low temperature or an excessively high temperature is not practical.

(2) Pyrolysis Reaction Conditions

A pyrolysis reaction of fluorine-containing methyl ether proceeds when fluorine-containing methyl ether is brought into contact with the catalyst described above in a gas phase in the presence of the catalyst. There is no particular limitation on the specific method. An example is a method in which the catalyst is placed in a tubular flow reactor, and fluorine-containing methyl ether used as a starting material is introduced to the reactor and brought into contact with the catalyst in a gas phase.

If the temperature of the pyrolysis reaction is excessively low, the conversion of the starting material tends to decrease. If the temperature of the pyrolysis reaction is excessively high, impurities tend to increase. Thus, the temperature of the pyrolysis reaction is preferably about 100 to 400° C., more preferably about 100 to 300° C., and particularly preferably about 100 to 250° C.

An excessively low pressure in the reaction tube during the pyrolysis reaction complicates the operation because of, e.g., the possible contamination of air, whereas an excessively high pressure in the reaction tube during the pyrolysis reaction requires that the pressure resistance of the equipment be considered and increases the possibility of leakage. Considering these points, the pressure in the reaction tube during the pyrolysis reaction is preferably about 0.05 to 1 MPa, more preferably about 0.1 to 0.5 MPa, and particularly preferably, in terms of reaction operation, about atmospheric pressure (about 0.1 MPa).

There is no particular limitation on the contact time for the reaction. The contact time is represented by W/F (g·sec/cc), i.e., the ratio of the amount of the catalyst W (g) relative to the flow rate F (the flow rate at 0° C. and 1 atm (about 0.1 MPa): cc/sec) of the starting material gas, i.e., fluorine-containing methyl ether, that is supplied to the reactor. The contact time is preferably about 1 to 100 g·sec/cc, more preferably about 1 to 50 g·sec/cc, and even more preferably about 5 to 30 g·sec/cc. If the contact time is too long, it takes a long time to obtain the product. To increase the amount of production, it is preferred that the contact time be shortened; however, if the contact time is too short, the conversion tends to decrease. Thus, the contact time may be selected so that the highest productivity is obtained in terms of the conversion of the starting material and the selectivity of the desired product, according to the type of catalyst to be used, the amount of the catalyst, the reaction conditions, and the like.

In general, it is desirable to conduct the reaction by selecting the contact time according to the type of catalyst to be used, the amount of the catalyst, the reaction conditions, and the like so that the conversion becomes 100%.

(3) Moisture Concentration or Moisture Removing Process

To achieve the effects of the present invention, the pyrolysis must be conducted under conditions with a low moisture concentration, specifically, 100 ppm or less.

As long as the effects of the present invention are obtained, there is no particular limitation. The pyrolysis is conducted at a moisture concentration of preferably 50 ppm or less, more preferably 30 ppm or less, and still more preferably 10 ppm or less.

The lower the water concentration, the more the effects of the present invention tend to improve under predetermined requirements. Therefore, in a way, it may be possible to understand that the effects of the present invention are achieved by removing moisture from the reaction system before or simultaneously with the pyrolysis, regardless of the final moisture concentration mentioned above. At this time, the method of the present invention is defined as a method comprising the step of removing moisture from the reaction system before or simultaneously with pyrolysis. In this step, preferably 90% or more, more preferably 95% or more, and still more preferably 99% or more moisture is removed from the reaction system.

In the above, there is no particular limitation on the method for controlling the moisture concentration to be within the above range or the method for removing moisture. Examples of such a method include a method that uses zeolite as a dehydrating agent, a method of rectifying and removing moisture, and the like. Alternatively, to control the moisture concentration to be within the above range, a starting compound may be used whose moisture concentration is initially adjusted to be within a predetermined range (i.e., dehydrated).

In the above, the reaction system is a closed space, in a precise sense, and refers to a reactor or the like.

(4) Catalyst Regeneration Treatment

In the method of the present invention, the catalytic activity may decrease with the lapse of the reaction time. In such cases, there is a possibility that the organic substance used as a starting material has been carbonized on the catalyst surface. When the catalytic activity decreases, the catalyst can be regenerated by allowing oxygen-containing gas to flow through the reaction tube with the catalyst being heated, reacting the carbon adhered to the catalyst surface with the oxygen to form gases such as carbon dioxide and carbon monoxide, and removing them. The temperature in the reactor during catalyst regeneration is preferably about 200 to 500° C., and more preferably about 300 to 400° C. As the oxygen-containing gas, it is efficient to use a high-purity gas; however, it is economically preferable to use air since a similar effect is obtained as long as the gas contains oxygen.

The time for catalyst regeneration varies depending on the type of catalyst and the time of use. The time for catalyst regeneration may be any time that can restore sufficient catalytic activity, and may be typically about 1 to 12 hours.

(5) At Least One Gas Selected from the Group Consisting of Hydrogen Fluoride, Chlorine, Hydrogen Chloride, and Air Further, in the present invention, the pyrolysis may be conducted in the presence of at least one gas selected from the group consisting of hydrogen fluoride, chlorine, hydrogen chloride, and air. This also makes it possible to extend the catalyst lifetime.

The hydrogen fluoride used for this purpose is preferably anhydrous hydrogen fluoride.

As long as the effect of extending the catalyst lifetime is achieved, there is no particular limitation. The pyrolysis is conducted in the presence of the gas mentioned above at a volume ratio of 0.03 or more, more preferably 0.05 or more, and even more preferably 0.10 or more, relative to the fluorine-containing methyl ether being taken as 1.

The higher the volume ratio of the gas mentioned above, relative to the fluorine-containing methyl ether being taken as 1, the more the effect of extending the catalyst lifetime tends to improve under predetermined requirements. Therefore, in a way, it may be possible to understand that the effects of the present invention are achieved by adding the gas mentioned above to the reaction system before or simultaneously with the pyrolysis, regardless of the final volume ratio above. At this time, the method of the present invention is defined as a method comprising the step of adding the gas to the reaction system before or simultaneously with pyrolysis. In this step, the gas mentioned above is added at a volume ratio of preferably 0.03 or more, more preferably 0.05 or more, and still more preferably 0.10 or more, relative to the fluorine-containing methyl ether being taken as 1.

In the above, the reaction system is a closed space, in a precise sense, and refers to a reactor or the like.

3. Reaction Product

A pyrolysis reaction of the fluorine-containing methyl ether is caused to occur by the method described above to obtain the desired fluoromethane and fluorine-containing compound.

There is no particular limitation on the method for separating the fluoromethane and fluorine-containing compound contained in the thus-obtained product. For example, the produced gas after the pyrolysis reaction may be cooled to separate it into a gas component comprising a low-boiling-point component that contains the fluoromethane (boiling point of −79° C.) as a main component, and a liquid component comprising a high-boiling-point component that contains the fluorine-containing compound as a main component and further may contain unreacted starting materials. In this case, the cooling temperature may be set in accordance with the difference in the boiling points of these components.

By the above method, the component containing the fluoromethane can be separated as a gas component. The gas component may contain propene (boiling point of −47.7° C.), pentafluoropropene (boiling point of −21.1° C.), propane (boiling point of −1.4° C.), etc., as impurities. However, these impurities are easily separated by distillation since fluoromethane and these impurities have very different boiling points.

In addition, when the high-boiling-point component, which is obtained as a liquid component and contains the fluorine-containing compound as a main component, contains unreacted starting materials, etc., the unreacted starting material, etc., can be easily separated by distillation.

With respect to the method for selectively obtaining fluoromethane, the product obtained after the pyrolysis reaction may be brought into contact with water, an aqueous alkaline solution, or the like to dissolve and remove the fluorine-containing compound in an aqueous phase. This enables the fluoromethane to be selectively obtained.

In the above process, an alcohol may be used instead of water or an aqueous alkaline solution. Inexpensive alcohols are preferable in terms of cost. Examples of usable alcohols include methanol, ethanol, propanol, and the like. Of these, methanol is particularly preferable. Bringing the product into contact with an alcohol to produce an ester makes combustion treatment easier.

With respect to the method for selectively obtaining the fluorine-containing compound from the pyrolyzed product, the product obtained by pyrolysis may be directly subjected to a distillation operation to remove fluoromethane as a column top component. In this manner, it may be sometimes possible to obtain the fluorine-containing compound as a column bottom component.

EXAMPLES

The present invention is described below in more detail with reference to Examples.

Example 1

Five hundred grams of molecular sieve 4 A was added to 1,1,3,3,3-pentafluoro-2-trifluoromethylpropylmethyl ether (OIME), and the mixture was stirred and dehydrated. The moisture in the OIME was appropriately measured by a Karl Fischer method, and dehydration was performed until the moisture content decreased to 100 ppm.

γ-alumina ($Al_2O_3$) that was not fluorinated was used as a catalyst and placed in a tubular metal reactor. This reaction tube was heated to 150° C., and the OIME that was dehydrated to 100 ppm was supplied to the reaction tube. Table 1 shows the amount of OIME treated per gram of catalyst and the change in conversion.

The outlet gas from the reaction tube was analyzed by gas chromatography. Table 1 shows the analytical results. The numerical values shown in Table 1 are the component proportions (%) determined by multiplying the area ratio of each peak obtained by the gas chromatography by a coefficient for correcting a sensitivity to each gas. In Table 1, "g-OIME/g-cat" refers to the amount of OIME treated per gram of catalyst, and "conv." refers to conversion.

The following terms represent the following compounds.
$CH_3F$: Fluoromethane
$C_3H_6$: Propene
HFC-1225zc: $CF_2=CHCF_3$
HFC-236fa: $CF_3CH_2CF_3$
Fluoride: 3,3,3-trifluoro-2-(trifluoromethyl)propanoly fluoride The low-boiling-point component containing $CH_3F$ and the high-boiling-point component containing fluoride were separately analyzed. The analytical results in Table 1 are proportions, expressed as percentages, of these components among the total components.

TABLE 1

| g-OIME/g-cat | conv. (%) | $CH_3F$ | $C_3H_6$ | HFC-1225zc | HFC-236fa | fluoride | Others | Total |
|---|---|---|---|---|---|---|---|---|
| 20 | 90.0 | 50.4 | 0.0002 | 0.1421 | 0.0211 | 49.2 | 0.1646 | 100 |
| 206 | 86.4 | 50.9 | 0.0003 | 0.0613 | 0.0229 | 48.9 | 0.1568 | 100 |
| 370 | 87.0 | 48.8 | 0.0003 | 0.1121 | 0.0325 | 51.0 | 0.1001 | 100 |
| 648 | 77.1 | 49.7 | 0.0003 | 0.0815 | 0.0146 | 49.9 | 0.2942 | 100 |
| 986 | 65.6 | 50.2 | 0.0033 | 0.0921 | 0.0181 | 48.9 | 0.8632 | 100 |
| 1189 | 57.7 | 50.4 | 0.0004 | 0.0823 | 0.0323 | 48.9 | 0.6667 | 100 |

Example 2

OIME was dehydrated to 5 ppm using the same method as Example 1. The resulting dehydrated OIME was supplied to a reaction tube using the same method as Example 1.

The outlet gas from the reaction tube was analyzed by gas chromatography. Table 2 below shows the analytical results.

TABLE 2

| g-OIME/g-cat | conv. (%) | $CH_3F$ | $C_3H_6$ | HFC-1225zc | HFC-236fa | fluoride | Others | Total |
|---|---|---|---|---|---|---|---|---|
| 17 | 99.8 | 49.2 | 0.0001 | 0.0223 | 0.0373 | 50.7 | 0.0403 | 100 |
| 215.1 | 99.9 | 49.3 | 0.0001 | 0.0329 | 0.1060 | 49.8 | 0.7581 | 100 |
| 531.8 | 99.9 | 49.1 | 0.0005 | 0.0824 | 0.0089 | 49.8 | 1.0133 | 100 |
| 870.8 | 99.9 | 50.0 | 0.0001 | 0.0222 | 0.0418 | 48.7 | 1.2176 | 100 |
| 1040.5 | 92.9 | 49.6 | 0.0001 | 0.0243 | 0.0321 | 49.9 | 0.4436 | 100 |
| 1192.9 | 88.4 | 49.5 | 0.0000 | 0.0264 | 0.0331 | 49.3 | 1.1404 | 100 |

Comparative Example 1

OIME was dehydrated to 500 ppm using the same method as Example 1. The resulting dehydrated OIME was supplied to a reaction tube using the same method as Example 1.

The outlet gas from the reaction tube was analyzed by gas chromatography. Table 3 below shows the analytical results.

TABLE 3

| g-OIME/g-cat | conv. (%) | $CH_3F$ | $C_3H_6$ | HFC-1225zc | HFC-236fa | fluoride | Others | Total |
|---|---|---|---|---|---|---|---|---|
| 23 | 99 | 49.9 | 0.0015 | 0.0292 | 0.0462 | 50.0 | 0.0231 | 100 |
| 176 | 93 | 50.0 | 0.0001 | 0.0190 | 0.0312 | 49.9 | 0.0497 | 100 |
| 548 | 72 | 50.0 | 0.0003 | 0.0242 | 0.0333 | 49.9 | 0.0421 | 100 |
| 176 | 93 | 50.0 | 0.0001 | 0.0190 | 0.0312 | 49.9 | 0.0497 | 100 |
| 548 | 72 | 50.0 | 0.0003 | 0.0242 | 0.0333 | 49.9 | 0.0421 | 100 |
| 880 | 50 | 49.6 | 0.0004 | 0.0971 | 0.0024 | 50.1 | 0.2001 | 100 |

The above results indicate that the less the moisture content in OIME, which is a starting material, the slower the rate of catalyst deterioration becomes.

Example 3

γ-alumina ($Al_2O_3$) that was not fluorinated was used as a catalyst and placed in a tubular metal reactor. This reaction tube was heated to 150° C., and 1,1,3,3,3-pentafluoro-2-trifluoromethylpropylmethyl ether (OIME), which is a starting material, was supplied to the reaction tube at a flow rate of 15 ccm/min, and hydrogen fluoride at a flow rate of 3.9 ccm/min (OIME/HF molar ratio=0.26).

Table 4 shows the amount of OIME treated per gram of catalyst and change in conversion.

The outlet gas from the reaction tube was analyzed by gas chromatography. Table 4 shows the analytical results. The numerical values shown in Table 4 are the component proportions (%) determined by multiplying the area ratio of each peak obtained by the gas chromatography by a coefficient for correcting a sensitivity to each gas.

The low-boiling-point component containing $CH_3F$ and the high-boiling-point component containing fluoride were separately analyzed. The analytical results in Table 4 are proportions, expressed as percentages, of these components among the total components. In Table 4, "g-OIME/g-cat" refers to the amount of OIME treated per gram of catalyst, and "conv." refers to conversion.

TABLE 4

| g-OIME/g-cat | conv. (%) | $CH_3F$ | $C_3H_6$ | HFC-1225zc | HFC-236fa | fluoride | Others | Total |
|---|---|---|---|---|---|---|---|---|
| 10 | 88.95 | 49.60 | 0.0001 | 0.01 | 0.01 | 49.20 | 1.2 | 100 |
| 242 | 96.83 | 49.40 | 0.0028 | 0.00 | 0.01 | 49.40 | 1.2 | 100 |
| 675 | 97.60 | 49.90 | 0.0082 | 0.02 | 0.03 | 49.54 | 0.5 | 100 |
| 826 | 98.06 | 50.40 | 0.0094 | 0.03 | 0.04 | 49.40 | 0.1 | 100 |
| 1024 | 97.71 | 47.89 | 0.0080 | 0.02 | 0.02 | 49.67 | 2.4 | 100 |

Example 4

1,1,3,3,3-Pentafluoro-2-trifluoromethylpropylmethyl ether, which is a starting material, was supplied to a reaction tube at a flow rate of 15 ccm/min, and hydrogen fluoride at a flow rate of 1.04 ccm/min (OIME/HF molar ratio=0.07), using the same method as Example 3. The outlet gas from the reaction tube was analyzed by gas chromatography using the same method as in Example 3. Table 5 shows the analytical results.

TABLE 5

| g-OIME/g-cat | conv. (%) | CH$_3$F | C$_3$H$_6$ | HFC-1225zc | HFC-236fa | fluoride | Others | Total |
|---|---|---|---|---|---|---|---|---|
| 32 | 86.3 | 49.5 | 0.0001 | 0.0403 | 0.0962 | 49.5 | 0.9 | 100 |
| 236 | 92.5 | 49.5 | 0.0026 | 0.0102 | 0.0603 | 50.2 | 0.2 | 100 |
| 809 | 93.0 | 49.2 | 0.0050 | 0.0120 | 0.0533 | 49.4 | 1.3 | 100 |
| 1068 | 94.0 | 49.6 | 0.0079 | 0.0182 | 0.0887 | 49.4 | 0.9 | 100 |
| 1218 | 93.0 | 49.7 | 0.0090 | 0.0203 | 0.0455 | 49.3 | 0.9 | 100 |

Comparative Example 2

1,1,3,3,3-Pentafluoro-2-trifluoromethylpropylmethyl ether, which is a starting material, was supplied alone to a reaction tube at a flow rate of 15 ccm/min using the same method as in Example 3, without supplying hydrogen fluoride. The outlet gas from the reaction tube was analyzed by gas chromatography using the same method as in Example 3. Table 6 shows the analytical results.

TABLE 6

| g-OIME/g-cat | conv. (%) | CH$_3$F | C$_3$H$_6$ | HFC-1225zc | HFC-236fa | fluoride | Others | Total |
|---|---|---|---|---|---|---|---|---|
| 20 | 90.0 | 50.4 | 0.0002 | 0.1421 | 0.0211 | 49.2 | 0.2 | 100 |
| 206 | 86.4 | 50.9 | 0.0003 | 0.0613 | 0.0229 | 48.9 | 0.2 | 100 |
| 370 | 87.0 | 48.8 | 0.0003 | 0.1121 | 0.0325 | 51.0 | 0.1 | 100 |
| 648 | 77.1 | 49.7 | 0.0003 | 0.0815 | 0.0146 | 49.9 | 0.3 | 100 |
| 986 | 65.6 | 50.2 | 0.0033 | 0.0921 | 0.0181 | 48.9 | 0.9 | 100 |
| 1189 | 57.7 | 50.4 | 0.0004 | 0.0823 | 0.0323 | 48.9 | 0.7 | 100 |

As described above, when HF was used in combination with 1,1,3,3,3-pentafluoro-2-trifluoromethylpropylmethyl ether (Tables 4 and 5), the decrease in conversion was moderate compared with a case in which HF was not used in combination (Table 6). These results clarify that a combined use of HF with 1,1,3,3,3-pentafluoro-2-trifluoromethylpropylmethyl ether makes it possible to extend the catalyst lifetime.

The invention claimed is:

1. A method for producing fluoromethane by pyrolyzing a fluorine-containing methyl ether represented by Formula (1) in a gas phase in the presence of a catalyst, the pyrolysis being conducted at a moisture concentration of 100 ppm or less,

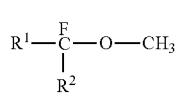

(1)

wherein R$^1$ and R$^2$ are identical or different, and each represents a substituted or unsubstituted straight or branched monovalent aliphatic hydrocarbon group, substituted or unsubstituted monovalent aromatic hydrocarbon group, substituted or unsubstituted monovalent cyclic aliphatic hydrocarbon group, hydrogen atom, or halogen atom.

2. A method for producing fluoromethane by pyrolyzing a fluorine-containing methyl ether represented by Formula (1) defined in claim 1 in the presence of a catalyst, the method comprising the step of removing moisture from the reaction system before or simultaneously with pyrolysis.

3. The method according to claim 1, wherein the catalyst is at least one member selected from the group consisting of metal oxides, fluorinated metal oxides, and metal fluorides.

4. The method according to claim 1, wherein the catalyst is at least one member selected from the group consisting of alumina, chromium oxide, titanium oxide, zinc oxide, fluorinated alumina, fluorinated chromium oxide, fluorinated titanium oxide, fluorinated zinc oxide, AlF$_3$, TiF$_4$, CrF$_3$, and ZnF$_2$.

5. The method according to claim 1, wherein the catalyst is alumina.

6. The method according to claim 4, wherein the alumina is γ-alumina.

7. The method according to claim 3, wherein the catalyst has a pore volume of 0.5 ml/g or more.

8. The method according to claim 1, wherein the temperature of the pyrolysis reaction is 100 to 400° C.

9. The method according to claim 1, wherein the pressure during the pyrolysis reaction is 0.05 to 1 MPa.

* * * * *